(12) United States Patent
Lozecznik

(10) Patent No.: US 11,470,793 B2
(45) Date of Patent: Oct. 18, 2022

(54) BACTERIAL STRAIN HAVING ANTI-FUNGAL PROPERTIES AND USES THEREOF

(71) Applicant: Kontzamanis Graumann Smith MacMillan Inc., Winnipeg (CA)

(72) Inventor: Stan Lozecznik, Winnipeg (CA)

(73) Assignee: Kontzamanis Graumann Smith MacMillan Inc., Winnipeg (CA)

( * ) Notice: Subject to any disclaimer, the term of this patent is extended or adjusted under 35 U.S.C. 154(b) by 0 days.

(21) Appl. No.: 17/279,811

(22) PCT Filed: Jan. 31, 2020

(86) PCT No.: PCT/CA2020/050114
§ 371 (c)(1),
(2) Date: Mar. 25, 2021

(87) PCT Pub. No.: WO2020/154813
PCT Pub. Date: Aug. 6, 2020

(65) Prior Publication Data
US 2021/0360890 A1    Nov. 25, 2021

Related U.S. Application Data

(60) Provisional application No. 62/799,838, filed on Feb. 1, 2019.

(51) Int. Cl.
| | |
|---|---|
| *A01N 63/25* | (2020.01) |
| *C12N 1/20* | (2006.01) |
| *A01H 3/00* | (2006.01) |
| *C12P 7/26* | (2006.01) |
| *C12P 17/08* | (2006.01) |
| *C12P 21/02* | (2006.01) |
| *A01G 22/15* | (2018.01) |
| *A01G 22/20* | (2018.01) |

(52) U.S. Cl.
CPC ............ *A01H 3/00* (2013.01); *A01N 63/25* (2020.01); *C12N 1/205* (2021.05); *C12P 7/26* (2013.01); *C12P 17/08* (2013.01); *C12P 21/02* (2013.01); *A01G 22/15* (2018.02); *A01G 22/20* (2018.02)

(58) Field of Classification Search
None
See application file for complete search history.

(56) References Cited

U.S. PATENT DOCUMENTS 7,935,335 B2     5/2011  Kochi et al.
2016/0278388 A1  9/2016  Beau et al.

FOREIGN PATENT DOCUMENTS

WO     2016020371    2/2016

OTHER PUBLICATIONS

Luo et al., "Complete Genome Sequence of Industrial Biocontrol Strain Paenibacillus polymyxa HY96-2 and Further Analysis of its Biocontrol Mechanism". Front Microbiol, Jul. 12, 2018, vol. 9, pp. 1520, ISSN 1664-302X.

*Primary Examiner* — David Steadman
(74) *Attorney, Agent, or Firm* — Michael R Williams; Ryan W Dupuis; Ade & Company Inc

(57) ABSTRACT

Described herein is the evaluation of the antifungal properties of bacterial strain KGS-3 against *Fusarium* Head Blight (FHB)) white mold, blackleg and a number of potato fungal diseases and the plant growth effect attained. KGS-3 is a novel strain of *Paenibacillus polymyxa* that can suppress bacterial and fungal plant diseases. KGS-3 is predicted to produce antifungal metabolites polymyxin, fusaricidin, and paenilarvin and has been demonstrated to produce cylindrol B. KGS-3 is a plant growth promoting bacteria demonstrated to increase protein content of plants and/or plant products.

11 Claims, 9 Drawing Sheets

NCGC00347666-02|2,4-dihydroxy-6-methyl-3-{(2E,4E)-3-methyl-5-{(1R,2R,6R)-1,2,6-trimethyl-3-oxocyclohexyl]penta-2,4-dienyl]benzaldehyde

BACTERIAL STRAIN HAVING ANTI-FUNGAL PROPERTIES AND USES THEREOF

PRIOR APPLICATION INFORMATION

The instant application is a 371 of PCT Application CA2020, filed Jan. 31, 2020, entitled "Bacterial Strain Having Anti-Fungal Properties and Uses Thereof", which claimed the benefit of U.S. Provisional Patent Application 62/799,838, filed Feb. 1, 2019, and entitled "Bacterial Strains Having Anti-Fungal Properties and Uses Thereof", the entire contents of which are incorporated herein by reference 5 for all purposes.

BACKGROUND OF THE INVENTION

Plant growth promoting bacteria (PGPB) benefit commercial crops by improving both yields and plant tolerance to stresses (high salinity, drought, etc.). Some PGPB possess other beneficial traits such as bioremediation of hydrocarbon and heavy-metal contaminated soils (Cheng et al. 2007). PGPB can interact with several economically important field crops including canola, soybean, wheat, and corn (Nehra et al. 2015). PGPB can promote higher crop yields and expedited or early crop emergence as well as improve growth under both stressed and optimal plant conditions (Cheng et al. 2007). This can occur from a variety of mechanisms including nutrient cross-feeding, modulation of plant stress hormones, and assistance in the creation of a beneficial rhizosphere environment to increase nutrient bioavailability (Nehra et al. 2015).

Wheat is Canada's largest crop and the single biggest export earner of all our agricultural products. In 2017, Canada produced more than 27 million tonnes of wheat, and was one of the top five wheat exporters. Canola is a major oilseed crop grown in temperate regions. In Canada, production acreage increased gradually from 6.5 to 22.9 million acres from 1986 to 2015. Concomitantly, total production of canola in Canada also increased from 3.7 to 21.3 million metric tonnes, making Canada one of the world's largest canola producers.

Soil-borne and stubble-borne fungal diseases of wheat and canola are recognized as one of the main obstacles for increasing production of these crops in Canada and around the world. Australian grain and oilseed industries have reported losses of over $250M annually. It is estimated that since 1990, wheat and barley farmers in the United States have lost over $3B dollars due to *Fusarium* Head Blight (FHB) epidemics. In Western Canada, the estimated impact of *Fusarium* between 1980 and 2009 was more than $1B.

For Canola, in 2009, China imposed new rules requiring Canadian exports to carry out certificates that proved the product was free of the disease. After the 2009 restrictions, Canada's loss was estimated at $1.3 B dollars (Globe and Mail 2016). In 2010, a year when conditions were favorable, *S. sclerotinia* (or white fungi) losses in Canada exceeded an estimated $600 M.

SUMMARY OF THE INVENTION

According to an aspect of the invention, there is provided a biologically pure culture of plant growth promoting bacteria KGS-3 *Paenibacillus polymyxa* strain deposited as IDAC 120719-01.

According to a further aspect of the invention, there is provided a method of increasing plant yield or preventing fungal infection of a plant or reducing severity of fungal infection of a plant comprising: inoculating an effective amount of plant growth promoting bacteria KGS-3 *Paenibacillus polymyxa* strain deposited as IDAC 120719-01 into a soil environment; and growing a plant in said soil environment, wherein said plant has increased plant yield compared to a plant of similar type grown in soil in the absence of plant growth promoting bacteria KGS-3 *Paenibacillus polymyxa* strain deposited as IDAC 120719-01.

According to a still further aspect of the invention, there is provided a method for increasing plant yield or preventing fungal infection of a plant or reducing severity of fungal infection of a plant comprising:

preparing a composition comprising a high-density aliquot of plant growth promoting bacteria KGS-3 *Paenibacillus polymyxa* strain deposited as IDAC 120719-01;

applying said composition to a soil environment in which seeds or seedlings have been or will be planted; growing said seeds or seedlings into plants in said soil environment, said plant growth promoting bacteria KGS-3 *Paenibacillus polymyxa* strain deposited as IDAC 120719-01 colonizing said soil environment and inhibiting fungal growth; and harvesting said plants.

According to a still further aspect of the invention, there is provided a method for increasing plant yield or preventing fungal infection of a plant or reducing severity of fungal infection of a plant comprising:

preparing a composition comprising a high-density aliquot of plant growth promoting bacteria KGS-3 *Paenibacillus polymyxa* strain deposited as IDAC 120719-01;

applying said composition to a growing plant in a soil environment; permitting continued growth of said growing plant in said soil environment, said plant growth promoting bacteria KGS-3 *Paenibacillus polymyxa* strain deposited as IDAC 120719-01 inhibiting fungal growth on the growing plant; and harvesting said plants.

In these embodiments, the high-density aliquot of plant growth promoting bacteria KGS-3 *Paenibacillus polymyxa* strain deposited as IDAC 120719-01 may be applied foliarly or may be formulated to be applied foliarly, that is, to the leaves and/or flowers of growing plants.

According to another aspect of the invention, there is provided a method of preventing or reducing the severity of *Fusarium* head blight in a cereal plant comprising:

preparing a high-density aliquot of plant growth promoting bacteria KGS-3 *Paenibacillus polymyxa* strain deposited as IDAC 120719-01;

applying said high-density aliquot to a growing cereal plant, a cereal seed or to a soil environment in which cereal seeds or cereal plant have been or will be planted;

growing said seeds, seedlings or plants in said soil environment, thereby producing a cereal crop, said plant growth promoting bacteria KGS-3 *Paenibacillus polymyxa* strain deposited as IDAC 120719-01 inhibiting fungal growth on said cereal crop; and harvesting said cereal crop.

According to another aspect of the invention, there is provided a method of preventing or reducing the severity of white mold in a plant comprising:

preparing a high-density aliquot of plant growth promoting bacteria KGS-3 *Paenibacillus polymyxa* strain deposited as IDAC 120719-01;

applying said high-density aliquot to a growing plant, a seedling, a seed or a soil environment in which seeds or seedlings have been or will be planted;

growing said seeds, seedlings or plants in said soil environment, thereby producing plants, said plant growth promoting bacteria KGS-3 *Paenibacillus polymyxa* strain deposited as IDAC 120719-01 inhibiting fungal growth on said plants; and harvesting said plants.

According to another aspect of the invention, there is provided a method of preventing or reducing the severity of blackleg in a *Brassicae* plant comprising:

preparing a high-density aliquot of plant growth promoting bacteria KGS-3 *Paenibacillus polymyxa* strain deposited as IDAC 120719-01;

applying said high-density aliquot to a growing *Brassicae* plant, a *Brassicae* seed, a *Brassicae* seedling or a soil environment in which *Brassicae* seeds or *Brassicae* plants have been or will be planted;

growing said seeds, seedlings or plants in said soil environment, thereby producing a *Brassicae* crop, said plant growth promoting bacteria KGS-3 *Paenibacillus polymyxa* strain deposited as IDAC 120719-01 inhibiting fungal growth on said *Brassicae* crop; and harvesting said *Brassicae* crop.

DESCRIPTION OF THE PREFERRED EMBODIMENTS

Figure 1:
FIG. 1 is a growth plate comparison of growth of KGS-3 and PA-23 (*Pseudomonas chlororaphis*) in the presence of (against) *Sclerotinia sclerotiorum* in duplicate.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "biologically pure" refers to a culture wherein virtually all of the cells present are of the selected strain.

As used herein, "inoculating" refers to introducing at least one bacterium into or onto a medium, for example, a liquid medium, granular product, carrier, peat powder, seed or a soil environment. For example, the bacterium may be coated on a seed or may be applied directly to the soil, as discussed herein As used herein, "soil environment" refers to the soil in which a plant is grown or is growing.

As used herein, "KGS-3" refers to a unique strain of *Paenibacillus polymyxa*, that is a facultative anaerobic Gram-positive bacteria, and that can suppress bacterial and fungal plant diseases. Specifically, *Paenibacillus polymyxa* KGS-3 refers to the strain deposited with the International Depositary Authority of Canada, National Microbiology Laboratory, Public Health Agency of Canada, 1015 Arlington Street, Winnipeg, Manitoba, Canada, R3E 3R2 under deposit number IDAC: 120719-01 on Jul. 12, 2019. As discussed herein, KGS-3 alone was also found to inhibit the growth of *Leptosphaeria maculans* (blackleg), *Sclerotinia sclerotiorum* (white mold), *Fusarium graminearum* 3ADON and *F. graminearum* 15 ADON chemotypes, as well as a number of potato fungal diseases, including Black Dot fungus, *Pythium* fungus, *Rhizoctonia*, *Alternaria solani* and *Veticillium*, as discussed below.

Described herein is the evaluation of the antifungal properties of bacterial strains isolated from fields in Southeastern Manitoba against *Fusarium graminearum* (*Fusarium* Head Blight (FHB)) for wheat and *Leptosphaeria maculans* (blackleg) for canola, and the plant growth effect attained.

*Fusarium* head blight, also called *Fusarium* ear blight or scab is a fungal disease of cereals such as for example wheat, barley, oats, rye and triticale. FHB is caused by a variety of fungi, including but by no means limited to *Fusarium avenaceum, Fusarium culmorum, Fusarium graminearum, Fusarium poae* and *Microdochium nivale*. The fungus infects the heads of the crop, reducing grain yield. The disease is often associated with contamination by mycotoxins produced by the fungi, discussed below.

*Fusarium graminearum* is the causal agent of *Fusarium* head blight or scab in wheat and causes up to 50% yield loss in addition to reduction of wheat protein quality. Moreover, *F. graminearum* produces trichothecene mycotoxins known as deoxynivalenol (DON) that can cause serious health problems in both human and animals. There are two types of chemotypes of *F. graminearum* that are prevalent in Manitoba (Guo et al, 2008) and North Dakota (Puri et al. 2010). They produce an acetyl ester derivative of DON at 15-position oxygen (15ADON) and an acetyl ester derivative of DON at 3-position oxygen (3ADON). The 3ADON chemotype is more virulent and produces more toxin than the 15ADON chemotype (Puri et al. 2010). 3-ADON chemotypes resulted in higher DON accumulation and a higher level of disease aggressiveness of the 3-ADON producers which was even observed in some wheat genotypes that were resistant to other ADON chemotype producers (Foroud et al., 2012). The complexity of the wheat genome is challenging to breeding programs and there is a need to reduce the use of chemical pesticides. Thus, it is important to develop a bio-control agent that can control 3ADON infection in wheat.

White mold is caused by *Sclerotinia sclerotiorum* and affects herbaceous, succulent plants such as flowers and vegetables. The fungus grows on the plant initially as pale to dark brown lesions on the stem proximal to the soil line prior to forming a white, fluffy, mycelial growth. Subsequently, other symptoms occur higher up in the plant, including chlorosis, wilting, and leaf drop.

Blackleg is caused by *Leptosphaeria macularis* which infects a variety of *Brassicae* crops including cabbage and canola.

As discussed herein, KGS strains were tested against *Fusarium* head blight, blackleg and white mold and a number of potato fungal diseases under controlled laboratory conditions. The tests were performed using petri dish assays with Potato Dextrose Agar (PDA), the fungi (*Fusarium, Leptosphaeria*, or *Sclerotinia*), a known antifungal bacteria strain (*Pseudomonas chlororaphis*), and ten (10) KGS strains. As discussed herein, the results indicated that KGS-3 has antifungal properties against *Fusarium* head blight, white mold, blackleg and several potato fungal diseases.

As discussed herein, KGS-3 is *Paenibacillus polymyxa*, a facultative anaerobic Gram-positive bacterium that can suppress bacterial and fungal plant diseases. The genus *Paenibacillus* phylogeny is based on 16S rRNA gene sequences previously classified as *Bacillus*. The genus *Paenibacillus* was subsequently reclassified into a separate family, Paenibacilliaceae (Padda et al., 2017). Some *P. polymyxa* are known to produce antibiotics that can suppress plant diseases. Moreover, *P. polymyxa* is considered a plant growth promoting bacteria (PGPB) (Raza et al, 2008).

Genome assembly was done using Pacbio's HGAP4 pipeline (smrtlink-release_6.0.0.47841) using the default parameters. The sequences were then blasted in NCBI nucleotide blast. Using this method, the best hit for KGS-3 is *Paenibacillus polymyxa* SC2. Annotation of the KGS-3 genome was done using prokka 1.13.3.

After annotation, the cpn60 of the genome was blasted in the cpn database. Based on this analysis, the most similar bacteria for KGS-3 are *Paenibacillus polymyxa* strains SC2 and M1. However, as discussed herein, there are significant differences between SC2, M1 and KGS-3.

PathogenFinder 1.1 with the option "automatic model selection" and "assembled genomes/contigs" (Costentino et al., 2013) revealed that KGS-3 is not a human pathogen.

Secondary metabolites produced by the three strains were analyzed with "antibiotics and secondary metabolite analysis shell" (antiSMASH). KGS3 was predicted to produce antifungal metabolites polymyxin, fusaricidin typical to *P. polymyxa* as well as the antifungal paenilarvin from other *Paenibacillus* species.

Specifically, the genome analysis of KGS-3 showed that KGS-3 has genes that produce antifungal compounds fusaricidin and paenilarvins (Iturin-Like Lipopeptide Secondary Metabolites) (Luo et al. 2018). Fusaricidins are a family of antifungal lipopeptides with a 15-guanidino-3-hydroxypentadecanoic acid (GHPD) as the fatty acid side chain and vary in their fatty acid part. In another study focused on the effect of fusaricidin on rot pathogen (*Pestalotiopsis*), it was found to affect energy supply for pathogen growth and disrupted pathogen-related material synthesis (Anming, 2017).

Macrobrevin is a recently discovered antibiotic and was predicted to be produced by KGS-3. Helfrich et al., 2018 found that macrobrevin is an antibiotically active chemical substance produced by the leaf colonizing bacteria *Brevibacillus* sp. Leaf182.

Marthiapeptide A is another antibacterial secondary metabolite predicted to be produced by KGS-3. Marthiapeptide has only been described once, from the marine thermophilic bacteria *Marinactinospora thermotolerans* SCSIO 00652 isolated from the China Sea (Zhou et al., 2012). This is believed to be the first report of the genes for the synthesis of this compound being found in a terrestrial organism. Zhou et al., 2012 reported that marthiapeptide A exhibits not only bactericidal effects but also cytotoxicity against human cancer cell lines.

Polymyxin is one of the primary antibiotics produced by *P. polymyxa* (Raza et al., 2008) and it is produced by KGS-3 as well.

In yet another study, the genomes of *Paenibacillus* species were found to produce antibacterial compounds tridecaptin A and paenicidins. Genes for production of these compounds were also found in the genome of KGS-3.

While not wishing to be bound to a particular theory or hypothesis, it is believed that the capacity of KGS-3 to produce these antibiotics make it more competitive for staying on the plant against non-fungicide-containing strains of bacteria, including closely related strains, thus making it more effective at surviving on the plants.

Specifically, as demonstrated in the Examples section, KGS-3 increased the protein content of crops grown in the presence of KGS-3 by 4% compared to an untreated control. That is, KGS-3 improves plant growth at least by increasing protein content. It is further noted that KGS-3 improves plant growth by increasing disease resistance of the plants, for example, by inhibiting fungal growth. This can be demonstrated a variety of ways, for example, by comparing damaged kernel percentage between a KGS-3-treated plant and an untreated control, as discussed herein.

Phylogeny of KGS-3 using cpn60 in relation to other *Paenibacillus* species was done using Neighbor-Joining method with 10,000 bootstrap replicates. The criteria to select the *Paenibacillus* species were that they were close hits to KGS-3 with the cpn60 database alignment. Similar to the NCBI whole genome blast and phylogeny, KGS-3 is closely related but distinct from strains SC2 and M1. Both the original (FIG. 11) and the bootstrap consensus tree (FIG. 12) confirm this.

In the phylogeny tree (FIG. 11), the percentage of replicate trees in which the associated taxa clustered together in the bootstrap test (10,000 replicates) are shown next to the branches (Felsenstien 1985). The tree is drawn to scale, with branch lengths in the same units as those of the evolutionary distances used to infer the phylogenetic tree. The evolutionary distances were computed using the Maximum Composite Likelihood method (Tamura et al., 2004) and are in the units of the number of base substitutions per site. This analysis involved 12 nucleotide sequences. Codon positions included were 1st+2nd+3rd+Noncoding. All ambiguous positions were removed for each sequence pair (pairwise deletion option). There was a total of 552 positions in the final dataset. Evolutionary analyses were conducted in MEGA X (Kumar et al., 2018).

Figure 12:
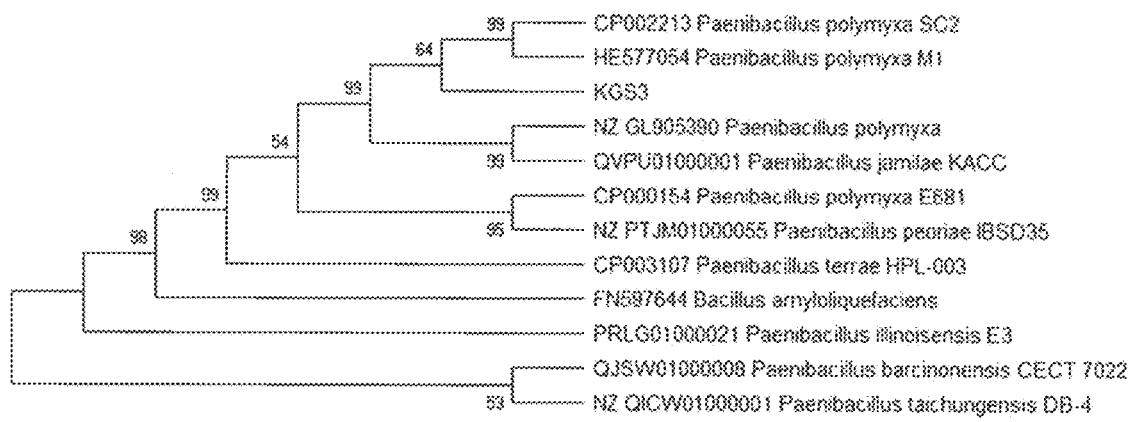
FIG. 12. The evolutionary history of KGS-3 inferred using the Neighbor-Joining method (Saitonu and Nei, 1987).
Figure 13:
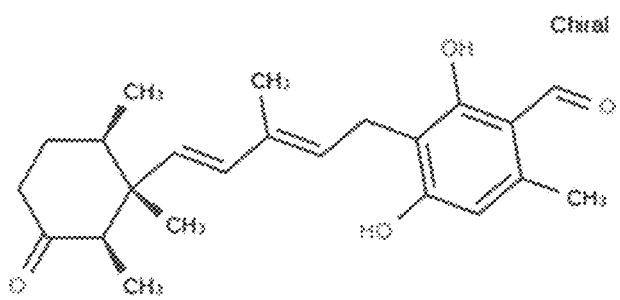
FIG. 13. Structure of 4-dihydroxy-6-methyl-3-[(2E,4E)-3-methyl-5-[(1R,2R,6R)-1,2,6-trimethyl-3-oxocyclohexyl]penta-2,4-dienyl]benzaldehyde (Cylindrol B).

The bootstrap consensus tree of KGS-3 phylogeny (FIG. 12) was inferred from 10000 replicates (Felsenstien 1985). This was taken to represent the evolutionary history of the taxa analyzed. Branches corresponding to partitions reproduced in less than 50% bootstrap replicates are collapsed. The percentage of replicate trees in which the associated taxa clustered together in the bootstrap test (10000 replicates) are shown next to the branches (Felsenstien 1985). The evolutionary distances were computed using the Maximum Composite Likelihood method (Tamura et al., 2004) and are in the units of the number of base substitutions per site. All ambiguous positions were removed for each sequence pair (pairwise deletion option). There was a total of 552 positions in the final dataset. Evolutionary analyses were conducted in MEGA X (Kumar et al., 2018).

The M1 strain NCBI accession numbers are HE577054.1 or NC 017542.1 and the NCBI accession numbers for strain SC2 are NC_014622.2 and CP002213.2.

antiSMASH resulted in similar clusters being found between KGS-3, M1 and SC2; however, there are some important differences.

For example, KGS-3 has the marthiapeptide A gene cluster whereas M1 and SC2 do not have this cluster.

Of the *P. polymyxa* plant growth promoting genes, KGS-3 has four phosphonate solubilizing genes from the phosphonate cluster: phnP, phnO, phnX and phnE. Out of these, only phnE is found in the genomes of M1 and SC2 (Eastman et al. 2014).

Of the phosphate transporters characteristic of plant growth promoting genomes, phoP, phoR, pstS, pstB and pstA are found in KGS-3, M1 and SC1. While pstC is found in M1 and SC1 but not in KGS-3, phosphate-specific transport system accessory protein PhoU was only found in KGS-3.

In addition, KGS-3 has the Hydrogen cyanide synthase subunit HcnC, which is characteristic of plant growth promoting bacterial genomes (Bruto et al 2014). However, HcnC is not found in M1 and SC1. Cyanide has been shown to have plant growth promoting effects in the rhizosphere by re-sequestering iron from iron-phosphate complexes, thereby making phosphate more available to the growing plant.

Dijksterhuis et al., 1999 found that the presence of living *P. polymyxa* bacteria was a prerequisite for continued suppression of fungal growth. Similarly, in the case of KGS-3, the unfiltered supernatant performed better than the filtered supernatant in a Petri plate assay against *F. graminearum*, as discussed herein. This suggests that the KGS-3 bacteria need to be present for enhanced antifungal activity, although, as discussed herein, the compounds are effective when isolated from the bacteria. Accordingly, as discussed herein, the supernatant from a KGS-3 growth culture may be used directly as an anti-fungal and/or antibacterial agent, or this supernatant may be used for the isolation and/or purification of anti-bacterial and/or anti-fungal compounds. As discussed herein, this anti-bacterial compound may be selected from the group consisting of macrobrevin, marthiapeptide A, tridecaptin A and paenicidins. This anti-fungal compound may be selected from the group consisting of polymyxin, fusaricidin, paenilarvin and cylindrol B. Furthermore, the anti-fungal and/or anti-bacterial agent or reagent may comprise at least one of macrobrevin, marthiapeptide A, tridecaptin A, paenicidins, polymyxin, fusaricidin, paenilarvin or cylindrol B and may be or may be prepared from KGS-3 growth media, as discussed herein.

As discussed below, effective antagonism of fungal growth by KGS-3 was not the result of competition for nutrients and was specific for *P. polymyxa* as demonstrated by using *E. coli* as a control along compared to KGS-3 in the assay, as discussed below.

While not wishing to be bound to a particular theory or hypothesis, the mechanism of the antifungal properties of KGS-3 may be production of: antifungal secondary metabolites; enzymes; extreme densities of bacteria around hyphal cells that may act as a nutrient sink, resulting in a weaker condition of the fungal cells; or a combination of all these mechanisms.

Suppression of hyphae growth by KGS-3 was also observed, as discussed herein. This has been observed in other antifungal bacteria as well. For example, Dijksterhuis et al., 1999, found that the formation of a bacterial nidus around hyphae was found to play an important role in the antagonistic interaction of *P. polymyxa* and fungi.

Specifically, a Petri plate growth assay carried out for 60 days at 4° C. clearly showed that KGS-3 suppressed hyphal growth. The KGS-3 cells survive at 4° C. This characteristic is important for performance of the bacteria for winter crops, particularly in view of the effectiveness of KGS-3 when applied early in plant growth, as discussed below. Specifically, because of its ability to grow at 4° C., KGS-3 can be applied to soil and/or growing crops even during or prior to predicted low temperatures.

Furthermore, as discussed herein, experiments demonstrated that growth of the bacteria prior to introduction of the fungus proved to be more effective at preventing fungal growth than experiments where fungi and bacteria were introduced simultaneously. Specifically, results indicated early application, for example at the start of flowering, or prior application of KGS-3, performed better than the late application or simultaneous application of KGS-3 in controlling the incidence of *F. graminearum* induced head blight on wheat. Specifically, as discussed herein, experiments on Petri plates and on plants indicate that the longer KGS-3 bacteria grow on and/or with the plant, the more effective they are at controlling fungal growth.

As such, in one embodiment of the invention, the high-density aliquot of KGS-3 is applied above ground, that is, onto the surface of a soil into which seeds and/or seedlings have been or will be planted. Alternatively, the high-density aliquot of KGS-3 may be applied to a growing plant, for example, to the leaves of the plant, or to the leaves and flowers of the plant after the plant has flowered. Alternatively, the high-density aliquot of KGS-3 may be applied to a growing plant after evidence of fungal disease has been observed.

As will be apparent to one of skill in the art, based on phylogenetic and genomic analysis, KGS-3 is a novel strain of *Paenibacillus polymyxa* that can suppress bacterial and fungal plant diseases. Specifically, as discussed herein, the effectiveness of KGS-3 against *Fusarium* head blight of wheat has been demonstrated. Furthermore, as discussed herein, KGS-3 is also predicted to produce at least the antifungal metabolites polymyxin and fusaricidin which is typical of *P. polymyxa* as well as the antifungal paenilarvin produced by other *Paenibacillus* species. Furthermore, as discussed herein, KGS-3 has been demonstrated to produce the anti-fungal compound cylindrol B.

FIG. 1 is a growth plate comparison of growth of KGS-3 (bottom) and PA-23 (top) (*Pseudomonas chlororaphis*) against *Scleronnia scleronorum*. As can be seen in this figure, while there is no zone of clearing around PA-23, even though this strain is known to produce the 2-hexyl, 5-propyl resorcinol (HPR). However, there is such a zone around KGS-3, indicating that this bacterial strain is capable of inhibiting growth of *Sclerotinia*.

Figure 2:
FIG. 2 shows growth plate comparison of growth of KGS-3 (duplicate) and a control in the presence of *Fusarium* after 3 days. View is from/of the bottom of the plates.

FIG. 2 shows growth plate comparison of growth of KGS-3 (duplicate) and a control in the presence of *Fusarium* after 3 days. View is from/of the bottom of the plates. *P. polymyxa* was streaked two times at equal distances on the potato dextrose agar plate, incubated for 24 hours at 30° C. and then actively growing mycelia of *F. graminearum* was placed at the center of the plate. The four replicates and the control further incubated at room temperature under constant light for three days. Photograph was taken from the bottom of the plate. The control was *F. graminearum* grown without the bacteria.

Figure 3:
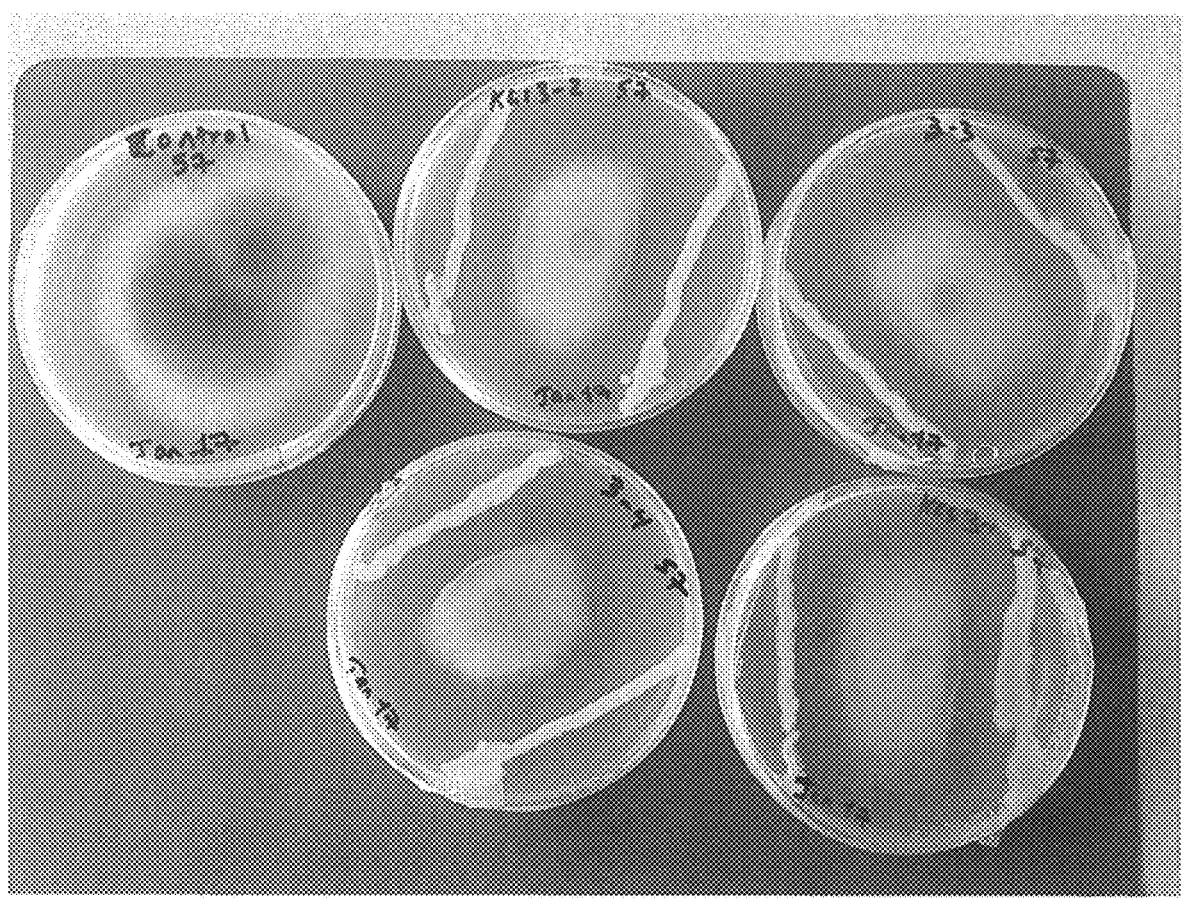
FIG. 3 shows growth plate comparison of growth of KGS-3 (quadruplicate) and a control in the presence of *Fusarium* after 3 days. View is from/of the top of the plates.

FIG. 3 shows growth plate comparison of growth of KGS-3 (quadruplicate) and a control in the presence of *Fusarium* after 3 days. View is from/of the top of the plates. *P. polymyxa* was streaked two times at equal distances on the potato dextrose agar plate and then actively growing mycelia of *F. graminearum* was placed at the center of the plate. The two replicates and the control were incubated at room temperature under constant light for three days. Photograph was taken from the bottom of the plate. The control was *F. graminearum* grown without the bacteria.

Figure 4:
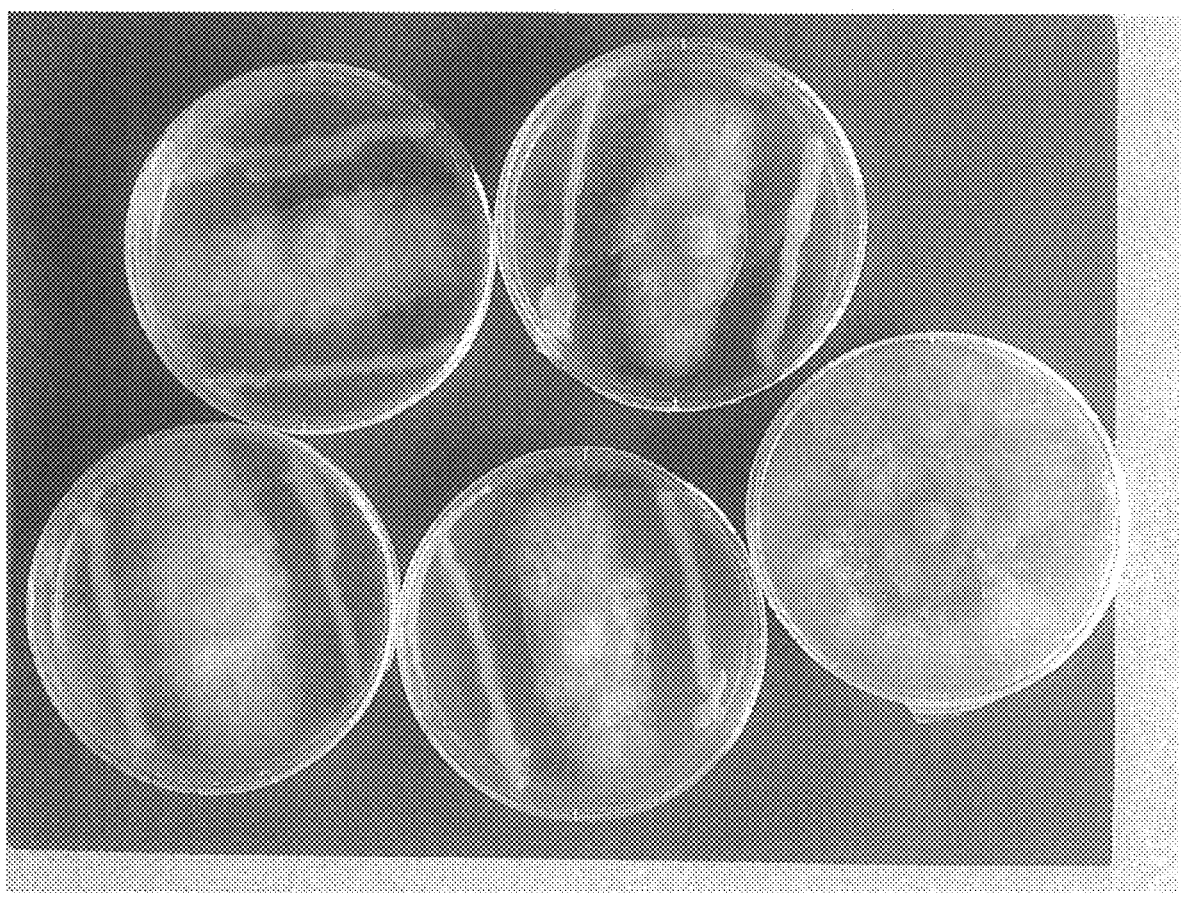
FIG. 4 shows growth plate comparison of growth of KGS-3 (quadruplicate) and a control in the presence of *Fusarium* after 4 days. View is from/of the top of the plates.

FIG. 4 shows growth plate comparison of growth of KGS-3 (quadruplicate) and a control in the presence of *Fusarium* after 4 days. View is from/of the top of the plates. Photograph of the same plates described below taken from the top of the plate.

Figure 5:
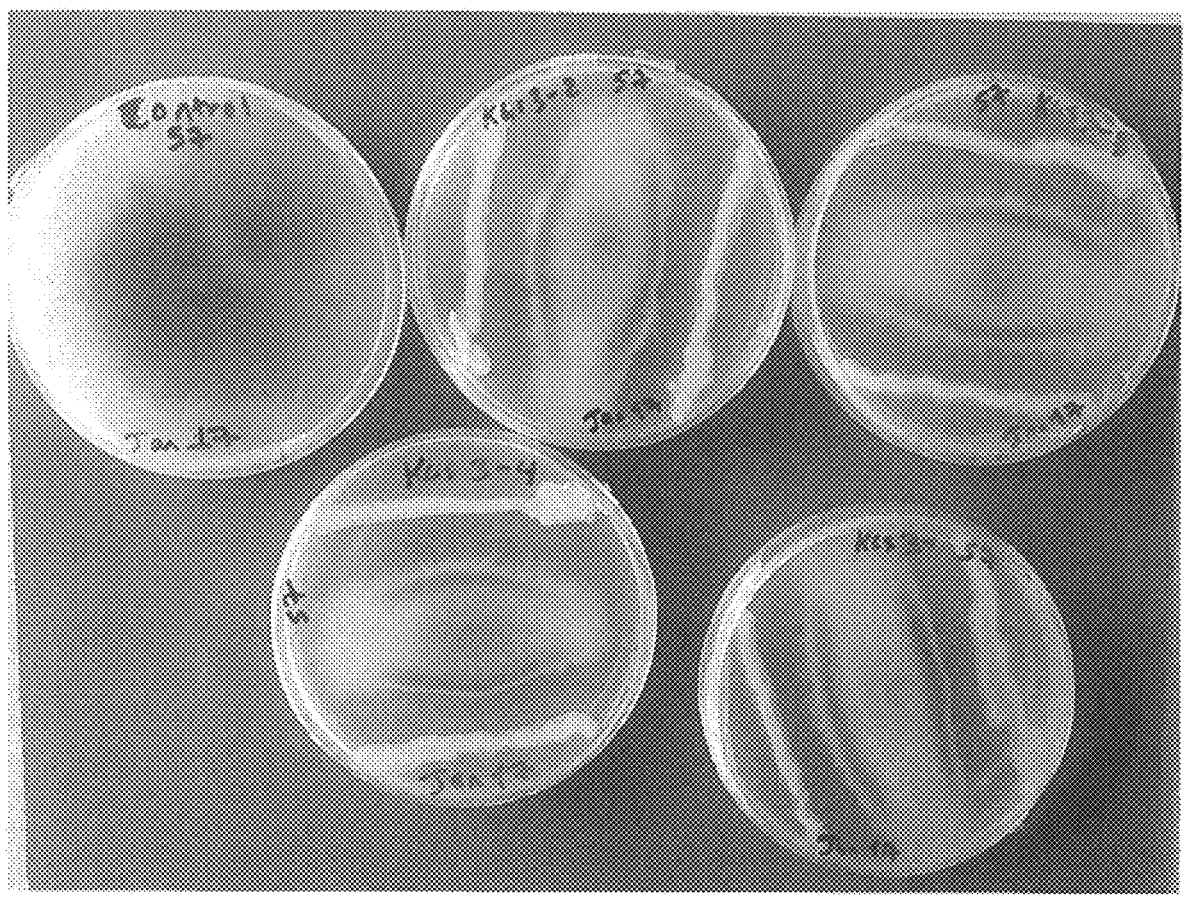
FIG. 5 shows growth plate comparison of growth of KGS-3 (quadruplicate) and a control in the presence of *Fusarium* after 3 days. View is from/of the bottom of the plates.

FIG. 5 shows growth plate comparison of growth of KGS-3 (quadruplicate) and a control in the presence of *Fusarium* after 3 days. View is from/of the bottom of the plates. *P. polymyxa* was streaked two times at equal distances on the potato dextrose agar plate, incubated for 24 hours at 30° C. and then actively growing mycelia of *F. graminearum* was placed at the center of the plate. The four replicates and the control further incubated at room temperature under constant light for four days. Photograph was taken from the bottom of the plate. The control was *F. graminearum* grown without the bacteria.

Figure 6:
FIG. 6 is a growth plate comparison of growth of KGS-3 and PA-23 (*Pseudomonas chlororaphis*) against *Leptosphaeria macularis* (blackleg).

FIG. 6 is a growth plate comparison of growth of KGS-3 and PA-23 (*Pseudomonas chlororaphis*) against *Leptosphaeria macularis* (blackleg). As can be seen, KGS-3 prevents *Leptosphaeria* growth.

As can be seen in this time course experiment, the fungal growth on the control plate increases significantly on the control plate between days 3 and 4. In contrast, the growth of the fungal colonies at the center of the KGS-3 plates show only a moderate increase in size and that increase is only between the "struck out" KGS-3 colonies/bacterial growth. That is, KGS-3 is clearly secreting anti-fungal compounds which prevent fungal growth in the areas surrounding KGS-3 growth.

Similar experiments were carried out wherein the ability of KGS-3 to inhibit growth of other species of fungi was tested. Specifically, a number of potato fungi were tested: Black Dot fungus, *Pythium* fungus, *Rhizoctonia, Alternaria solani* and *Veticillium*. Similar results were obtained, indicating that KGS-3 has broad activity against a wide variety of fungi and as such can be considered as a general anti-fungal.

Figure 7:
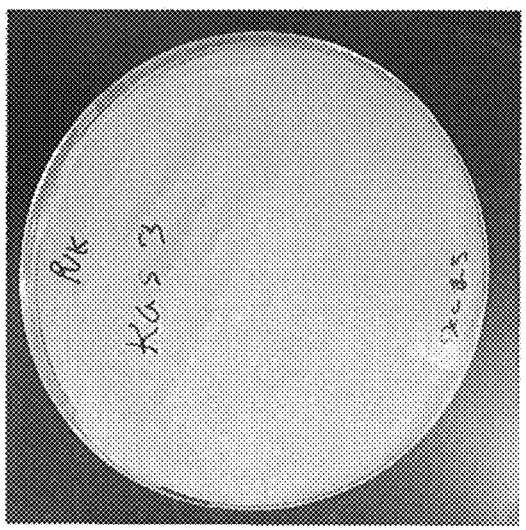
FIG. 7. KGS-3 was streaked onto PVK plates and incubated at 30° C. The PVK medium is white due to the insoluble calcium phosphate but there was a clearing of the phosphate that is a transparent zone around the bacterial colonies.

FIG. 7 shows growth of KGS-3 on Pikovskaya's (PVK) media, which contains insoluble calcium phosphate. KGS-3 was streaked onto the PVK plates and incubated at 30° C. The PVK medium is white where there is insoluble calcium phosphate; however, solubilization of the phosphate by KGS-3 can be visualized on these plates as the formation of a transparent zone around the bacterial colonies.

Figure 8:
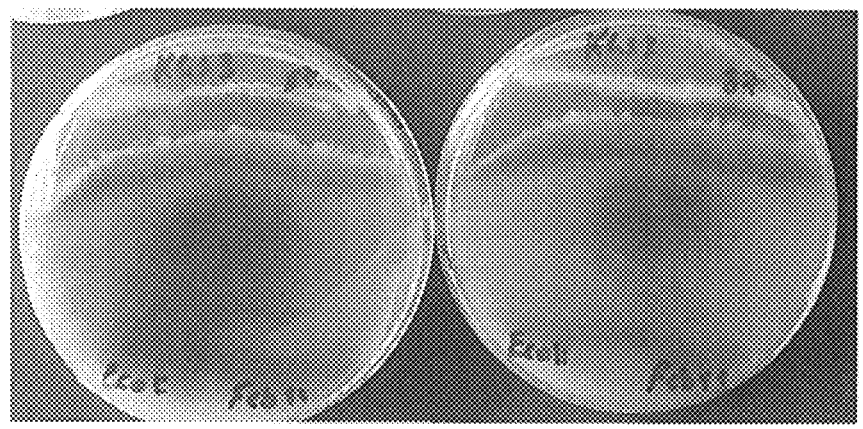
FIG. 8. Experiment to demonstrate that the zone of clearing is not due to nutrient depletion by the bacteria. *E. coli* which has no antifungal effects and was used as a control. *F. graminearum* strain 87 (3 ADON with higher DON toxin production) grew over *E. coli* (bottom of plates). However, *F. graminearum* did not overgrow on KGS-3 (Top of plates). The bacteria and the fungus were incubated at room temperature under constant light for four days.
Figure 9:
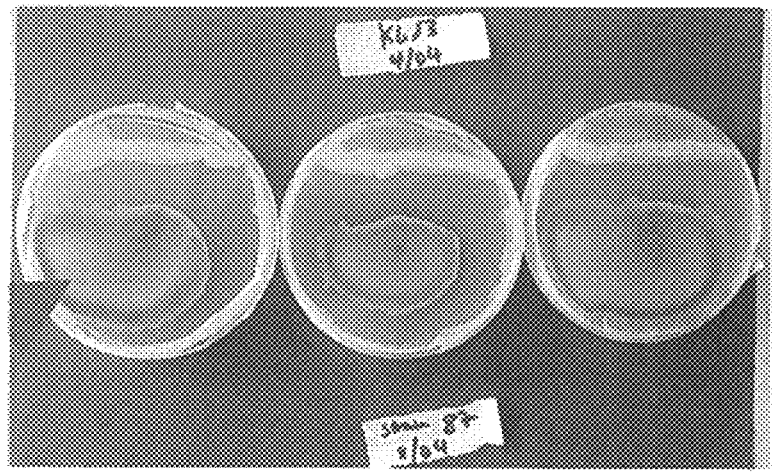
FIG. 9. Culture of KGS-3, and *Fusarium graminearum* strain 87 for 60 days. Still no hyphae grew over KGS 3.

FIG. 8 shows a comparison of the growth of KGS-3, and an *E. coli* strain that has no anti-fungal activities. The bacterial strains were struck out on Petri plates containing suitable growth media and then *F. graminearum* strain 87 (3 ADON with higher DON toxin production) was introduced. As can be seen, *F. graminearum* grew over *E-coli* (lower portion of plates) but KGS-3 prevented fungal growth, which can be seen as a clearing on the side of KGS-3 (upper portion of plates). The bacteria and the fungus were incubated at room temperature under constant light for four days.

The breakthrough result proving that KGS-3 is effective in controlling the growth of the fungus was demonstrated following storage of the plates from the assay shown in FIG. 5 kept at 4° C. for 60 days (FIG. 9). As can be seen, despite the long incubation time and the low temperature, KGS-3 prevents growth of the fungus. As discussed herein, this indicates that KGS-3 can be applied to plants and/or soil at low temperatures and still act as an effective anti-fungal agent.

FIG. 10 shows the effect of fractions derived from the supernatant recovered from a KGS-3 culture on fungal growth. In this experiment, a high toxin producing strain of *F. graminearum* also known as 3ADON was grown on a Petri plate that had previously been prepared for administration of supernatants by cutting equal sized holes in the agar of the growth media at equal distances from the center of the Petri plate. During the experiment, a disk comprising 3ADON was placed at the center of the petri plate and a drop of supernatant was put into each well. As can be seen, different fractions of KGS-3 supernatant were applied to the plate and one fraction, containing a compound identified as cylindrol B, showed a clearing of fungus around the well (FIG. 10).

According to an aspect of the invention, there is provided a biologically pure culture of KGS-3, that is, of plant growth promoting bacteria KGS-3 *Paenibacillus polymyxa* strain deposited as IDAC 120719-01.

According to a further aspect of the invention, there is provided a method of increasing plant yield or preventing fungal infection of a plant or reducing severity of fungal infection of a plant comprising: inoculating an effective amount of KGS-3 into a soil environment; and growing a plant in said soil environment, wherein said plant has increased plant yield compared to a control plant of similar type grown under similar conditions except for the presence of KGS-3. That is, the control plant of similar type is grown under similar conditions except that KGS-3 is not present. It is of note that this control does not necessarily need to be repeated each time.

As discussed herein, KGS-3 has been demonstrated to increase protein content of plants. Furthermore, KGS-3 is known to produce a number of anti-bacterial and anti-fungal compounds, including cylindrol B. These compounds will at least inhibit fungal growth, which will in turn reduce the severity of fungal infection, in some cases, by preventing fungal infection from occurring. This has been demonstrated by the inhibition of fungal growth on Petri plates, as discussed herein, and also by a reduction in damaged kernel percentage compared to suitable controls, as discussed herein.

According to a still further aspect of the invention, there is provided a method for increasing plant yield or protein content of a plant or plant product or preventing fungal infection of a plant or reducing severity of fungal infection of a plant comprising:

preparing a composition comprising a high-density aliquot of plant growth promoting bacteria (PGPB) KGS-3;

applying said composition to a soil environment in which seeds or seedlings have been or will be planted; growing said seeds or seedlings into plants in said soil environment, said PGPB KGS-3 colonizing said soil environment and inhibiting fungal growth; and harvesting said plants.

In some embodiments, the severity of fungal infection is reduced or the plant yield or the plant or plant product protein content is increased compared to a control plant of similar type grown under similar conditions except for the presence of KGS-3. That is, the control plant of similar type is grown under similar conditions except that KGS-3 is not present. It is of note that this control does not necessarily need to be repeated each time.

According to a still further aspect of the invention, there is provided a method for increasing plant yield preventing fungal infection of a plant or reducing severity of fungal infection of a plant comprising:

preparing a composition comprising a high-density aliquot of plant growth promoting bacteria (PGPB) KGS-3;

applying said composition to a growing plant in a soil environment; permitting continued growth of said growing plant in said soil environment, said PGPB inhibiting fungal growth on the growing plant; and harvesting said plants.

In some embodiments, the severity of fungal infection is reduced and/or the plant yield is increased compared to a control plant of similar type grown under similar conditions except for the presence of KGS-3. That is, the control plant of similar type is grown under similar conditions except that KGS-3 is not present. It is of note that this control does not necessarily need to be repeated each time.

In these embodiments, the high-density aliquot of KGS-3 may be applied foliarly or may be formulated to be applied foliarly, that is, to the leaves and/or flowers of a growing plant. Specifically, as discussed herein, in some embodiments, the high-density aliquot of KGS-3 and/or anti-fungal and/or anti-bacterial compounds produced by KGS-3 may be applied to growing plants, for example, to leaves and/or flowers of the growing plants. In some embodiments, the high-density aliquot of KGS-3 and/or the anti-fungal and/or anti-bacterial compounds produced by KGS-3 may be applied to a growing plant after the growing plant has entered the flowering stage and/or after evidence of fungal infection has been detected.

Furthermore, as discussed herein, KGS-3 is capable of producing several anti-bacterial and anti-fungal compounds and while not wishing to be bound to a particular theory or hypothesis, it is believed that at least one way in which KGS-3 inhibits fungal growth and/or prevents fungal infection and/or reduces severity of a fungal infection is by the secretion of these anti-fungal compounds, for example, at least one of polymyxin, fusaricidin, paenilarvin and/or cylindrol B. As discussed herein, growth of KGS-3 on these plants will result in the secretion of anti-bacterial and anti-fungal compounds, which will in turn inhibit fungal growth and/or prevent fungal growth and/or reduce severity of a fungal infection, thereby improving or increasing plant growth. Furthermore, as discussed herein, KGS-3 is capable of secreting these compounds even at low temperatures.

As such, in one aspect of the invention, a method of increasing plant growth and/or reducing fungal infection and/or reducing fungal damage to a growing plant includes the steps of applying the high density aliquot of KGS-3 to a growing plant, allowing the KGS-3 to grow on the growing plant, said KGS-3 secreting anti-fungal compounds, thereby reducing severity of a fungal infection of the growing plant.

According to another aspect of the invention, there is provided a method of preventing or reducing the severity of *Fusarium* head blight in a cereal plant comprising:

preparing a high-density aliquot of plant growth promoting bacteria (PGPB) KGS-3;

applying said high-density aliquot to a growing cereal plant, a cereal seed or to a soil environment in which cereal seeds or cereal plant have been or will be planted;

growing said seeds, seedlings or plants in said soil environment, thereby producing a cereal crop, said PGPB KGS-3 inhibiting fungal growth on said cereal crop; and harvesting said cereal crop.

The *Fusarium* head blight may be caused by a fungus selected from the group consisting of *Fusarium avenaceum, Fusarium culmorum, Fusarium graminearum, Fusarium poae* and *Microdochium nivale*.

In some embodiments, the cereal crop is selected from the group consisting of wheat, barley, oats, rye or triticale.

In some embodiments, the severity of the *Fusarium* infection is reduced and/or the plant yield is increased compared to a control plant of similar type grown under similar conditions except for the presence of KGS-3. That is, the control plant of similar type is grown under similar conditions except that KGS-3 is not present. It is of note that this control does not necessarily need to be repeated each time.

According to another aspect of the invention, there is provided a method of preventing or reducing the severity of white mold in a plant comprising:

preparing a high-density aliquot of plant growth promoting bacteria (PGPB) KGS-3;

applying said high-density aliquot to a growing plant, a seedling, a seed or a soil environment in which seeds or seedlings have been or will be planted;

growing said seeds, seedlings or plants in said soil environment, thereby producing plants, said PGPB KGS-3 inhibiting fungal growth on said plants; and harvesting said plants.

In some embodiments, the white mold is caused by *Sclerotinia sclerotiorum*.

In some embodiments, the severity of white mold is reduced or the plant yield is increased compared to a control plant of similar type grown under similar conditions except for the presence of KGS-3. That is, the control plant of similar type is grown under similar conditions except that KGS-3 is not present. It is of note that this control does not necessarily need to be repeated each time.

According to another aspect of the invention, there is provided a method of preventing or reducing the severity of blackleg in a *Brassicae* plant comprising:

preparing a high-density aliquot of plant growth promoting bacteria (PGPB) KGS-3;

applying said high-density aliquot to a growing *Brassicae* plant, a *Brassicae* seed, a *Brassicae* seedling or a soil environment in which *Brassicae* seeds or *Brassicae* plants have been or will be planted;

growing said seeds, seedlings or plants in said soil environment, thereby producing a *Brassicae* crop, said PGPB KGS-3 inhibiting fungal growth on said *Brassicae* crop; and harvesting said *Brassicae* crop.

In some embodiments, the severity of the blackleg infection is reduced or the plant yield is increased compared to a control plant of similar type grown under similar conditions except for the presence of KGS-3. That is, the control plant of similar type is grown under similar conditions except that KGS-3 is not present. It is of note that this control does not necessarily need to be repeated each time.

In some embodiments, the fungus is *Leptosphaeria maculariss* (blackleg).

According to another aspect of the invention, there is provided a method of preventing or reducing the severity of potato fungal infection of a potato plant comprising:

preparing a high-density aliquot of plant growth promoting bacteria (PGPB) KGS-3;

applying said high-density aliquot to a growing potato plant or a soil environment in which potato plants have been or will be planted;

growing said potato plants in said soil environment, thereby producing a potato crop, said PGPB KGS-3 inhibiting fungal growth on said potato crop; and harvesting said potato crop.

In some embodiments, the severity of the fungal infection is reduced and/or the potato plant yield and/or the potato or potato plant protein content is increased compared to a control potato plant grown under similar conditions except for the presence of KGS-3. That is, the control potato plant is grown under similar conditions except that KGS-3 is not present. It is of note that this control does not necessarily need to be repeated each time.

As such, a high-density aliquot of KGS-3 is used for promoting or improving plant yield by inhibiting fungal growth in the soil environment and/or on the growing plant, as discussed herein.

In some embodiments, the improvement or promotion of plant growth is compared to a control plant of similar type grown under similar conditions except for the presence of KGS-3. That is, the control plant of similar type is grown under similar conditions except that KGS-3 is not present. It is of note that this control does not necessarily need to be repeated each time.

As will be appreciated by one of skill in the art, the high-density aliquot refers to what is essentially an effective amount of KGS-3 for promoting or improving or increasing yield of a plant or for reducing or preventing crop damage from fungal infection. As discussed herein, an effective amount will depend on several factors, including the type and/or variety of the plant, the type of soil and in particular the concentration and type of nutrients present in the soil, the growth conditions expected to be encountered by the plants during their life cycle and the type of fungi that the plant may encounter during growth (as well as the growth conditions likely to be encountered by fungi during the plants' growth cycle).

Accordingly, as used herein, a high-density aliquot refers to an aliquot that has at least $10^3$ colony forming units per ml or at least $10^4$ colony forming units per ml, or at least $10^5$ colony forming units per ml or at least $10^6$ colony forming units per ml or at least $10^7$ colony forming units per ml or at least $10^8$ colony forming units per ml or at least $10^9$ colony forming units per ml or at least $10^{10}$ colony forming units per ml. In some preferred embodiments, a high-density aliquot is at least $10^5$ colony forming units per ml or at least $10^6$ colony forming units per ml.

Specifically, administration of a high-density aliquot of the bacteria is essential for the establishment of a culture that can colonize the rhizosphere of the growing plant and/or impair or reduce fungal growth and/or prevent or reduce fungal infection on the surface of the plant. This is necessary for survival of the bacteria in the soil environment because of the presence of competitors and predators, as discussed below.

Specifically, in their natural environment, KGS-3 is beset by predators and competitors, making it impossible for the establishment of a culture of sufficient density to convey beneficial effects on plants growing within the soil environment. Specifically, KGS-3 must not only compete with other bacteria for nutrients, the bacteria are also beset by protozoa, worms, arthropods and bacteriophage which will eat or infect/lyse the bacteria, thereby significantly reducing numbers of the bacteria and/or limiting the ability of the bacteria to establish within the soil.

Accordingly, in some embodiments of the invention, a high-density aliquot of KGS-3 is applied to the soil either immediately prior to planting, simultaneously with planting, or immediately after planting. In other embodiments, the high-density aliquot may be applied to a seed as a coating or foliar to a growing plant or seedling that may or may not have been planted in a soil environment at the time of application.

The application of this high-density aliquot can be done as liquid suspension or as solid materials applied to soil, potting mixture, seeds, seed pieces, seedlings, foliage, carrier materials, roots and planting soil. For example, KGS-3 may be coated onto a seed or seed piece, may be applied as a powder, may be applied as a liquid, may be applied foliar or as a suspension to a soil environment or may be mixed into a soil environment prior to use of the soil environment for planting.

As discussed herein, the high-density aliquot may be a known concentration or density of KGS-3 suspended in a suitable liquid, for example, a suitable buffer or application solution or agriculturally-acceptable or agriculturally-compatible oil, and applied as a foliar fungicide on growing plants, as discussed herein. Alternatively, the high-density liquid aliquot may be KGS-3 suspended in suitable culture media, which as will be appreciated by one of skill in the art would also include anti-bacterial and anti-fungal compounds secreted by KGS-3.

In some embodiments of the invention, the high-density aliquot may be administered to the soil or plant or seed as a liquid or a powder, for example at a density of at least $10^3$, $10^4$, $10^5$, $10^6$, $10^7$, $10^8$, $10^9$ or $10^{10}$ colony forming units per ml.

In other embodiments, the high-density aliquot may be applied to a carrier and then applied to the soil for example but not necessarily as a powder. As discussed herein, the carrier may be is a seed wherein KGS-3 is coated onto the seed. In some embodiments, the seed may be coated with peat or clay or mineral or vermiculite or polymer prior to application of a high-density liquid aliquot. Alternatively, a carrier such as peat, clay, diatomaceous earth, a mineral, vermiculite, perlite granule, a polymer or the like may be mixed with a high-density liquid aliquot and then dried, as discussed herein. The dried carrier comprising the high-density aliquot may then be applied to the seed or to the soil, as discussed herein.

Figure 10:
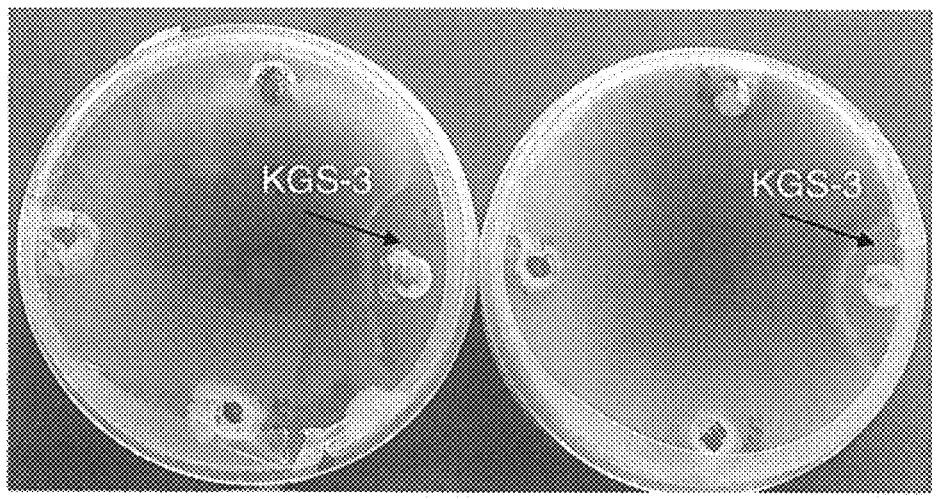
FIG. 10. A fraction from the supernatant isolated from a culture of KGS-3 showed clearing against fungus when applied to a petri plate.
Figure 11:
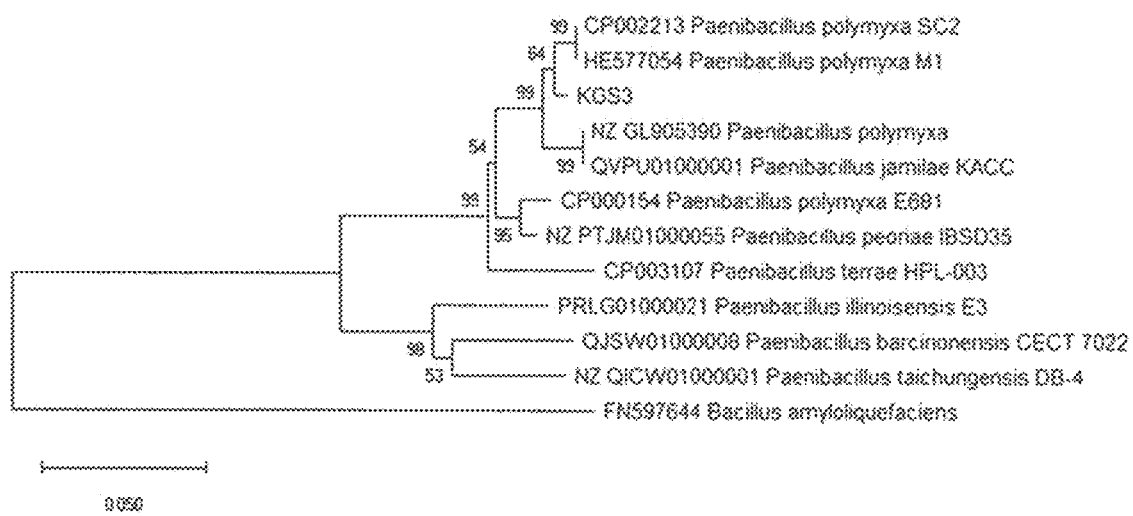
FIG. 11. The evolutionary history of KGS-3 was inferred using the Neighbor-Joining method (Saitonu and Nei, 1987). The optimal tree with the sum of branch length=0.55467894 is shown.

As discussed above, KGS-3 secretes at least one compound that has anti-fungal properties which prevent fungal growth, as discussed herein and as shown in FIGS. 1-6 and especially in FIG. 10. As will be appreciated by one of skill in the art, the isolation and enrichment and/or purification of compounds from bacteria is well-established. For example, KGS-3 can be grown in culture media and the cells spun down or otherwise separated from the supernatant. The supernatant can then be fractionated using any one or more of a variety of fractionation schemes to identify specific fractions which retain anti-fungal activity. As will be apparent to one of skill in the art, the anti-fungal properties of suitable fractions may be exploited directly and/or may be used for further purification and/or isolation. Accordingly, an effective amount of KGS-3 and/or the anti-fungal compounds secreted by KGS-3 may be used to prevent a fungal infection or to reduce the severity of a fungal infection, as discussed herein.

Specifically, as discussed above, KGS-3 is capable of secretion of a number of antifungal and/or antibacterial secondary metabolites, including but by no means limited to: marthiapeptide A; macrobrevin; tridecaptin A; paenicidin; polymyxin; fusaricidin; paenilarvin; and cylindrol B. In an exemplary example, production of cylindrol B from KGS-3 is described; however, it is to be understood that any of the compounds secreted by KGS-3 or combinations thereof may be isolated from the growth media of KGS-3, as discussed herein.

Specifically, as discussed below, the supernatant from a KGS-3 culture was isolated and analyzed. Analysis revealed the presence of at least 11 unique compounds. These compounds were separated and purified and tested for activity against *Fusarium*. The anti-*Fusarium* activity was associated with one fraction and subsequent analysis identified that compound as having characteristics that were consistent with the compound being cylindrol B, as discussed below.

According to another aspect of the invention, there is provided a method of producing an antifungal or antibacterial composition comprising:

growing KGS-3 bacterial cells in a suitable liquid growth medium to a suitable culture density;

separating the liquid growth medium into KGS-3 bacterial cells and a supernatant; and recovering the supernatant for use as an anti-fungal and/or antibacterial composition.

In some embodiments of the invention, the supernatant is processed, for example, concentrated and/or fractionated so that the processed supernatant is enriched for one or more of the anti-fungal or anti-bacterial compounds compared to the unprocessed supernatant.

In yet other embodiments, one or more of the anti-fungal and/or anti-microbial compounds in the supernatant is isolated and/or purified from the supernatant. These anti-fungal and/or anti-microbial compounds may be combined separately or in various combinations with a suitable carrier and/or diluent, for example, an agriculturally or agronomically acceptable carrier and/or diluent, to produce the antifungal and/or anti-microbial composition.

According to another aspect of the invention, there is provided a method of producing cylindrol B comprising:

growing KGS-3 bacterial cells in a suitable liquid growth medium to a suitable culture density;

separating the liquid growth medium into KGS-3 bacterial cells and a supernatant; and recovering cylindrol B from the supernatant.

In some embodiments, the cylindrol B is isolated and/or purified from the supernatant. As will be appreciated by one of skill in the art, "isolated" refers to removal of the compound from its native milieu, in this case, from the growth media, that is, the supernatant. As used herein, "purification" does not require absolute purity, but merely requires that for example the cylindrol B is enriched, that is, that the concentration of the cylindrol B is increased relative to the concentration of cylindrol B in the supernatant, for example, by 2 fold, by 5 fold, by 10 fold or by 100 fold or more.

It is noted that suitable methods for purification and/or isolation of the anti-fungal and/or anti-bacterial compounds, including but not limited to cylindrol B, will be readily apparent to one of skill in the art of general chemistry and can be determined and/or optimized through routine experimentation.

As discussed herein, a suitable culture density may be a bacterial growth culture that comprises at least $10^3$ colony forming units per ml or at least $10^4$ colony forming units per ml, or at least $10^5$ colony forming units per ml or at least $10^6$ colony forming units per ml or at least $10^7$ colony forming units per ml or at least $10^8$ colony forming units per ml or at least $10^9$ colony forming units per ml or at least $10^{10}$ colony forming units per ml.

As discussed herein, KGS-3 can be grown in any one of a variety of suitable bacterial growth media known in the art. For example, as discussed herein, KGS-3 can be grown in LB medium.

As will be appreciated by one of skill in the art, experimentation has determined that KGS-3 grows better in baffled flasks than normal flasks. While not wishing to be bound to a particular theory or hypothesis, it is believed that the oxygen transfer to the bacteria is improved when baffled flasks are used.

It was also determined that the addition of fresh media to a culture of growing KGS-3 bacteria improved the yield of secondary metabolites.

As discussed above, KGS-3 also has four phosphonate solubilizing genes from the phosphonate cluster: phnP, phnO, phnX and phnE.

KGS-3's genome also comprises phosphate transporters phoP, phoR, pstS, pstB and pstA and phosphate-specific transport system accessory protein PhoU.

Finally, KGS-3 has the Hydrogen cyanide synthase subunit HcnC, which is characteristic of plant growth promoting bacterial genomes.

It is believed that the combination of phosphonate-solubilizing, phosphate transporter and hydrogen cyanide synthase subunit genes that is unique to KGS-3 compared to SC2 and M1 means that this bacterial strain is better suited for plant growth promotion, as discussed herein.

As will be appreciated by one of skill in the art, KGS-3 may be combined with one or more suitable PGPB known in the art.

The invention will now be further explained and/or elucidated by way of examples; however, the invention is not necessarily limited to the examples.

Example 1: Petri Plate Fungal Growth Experiments

As shown in FIGS. 1-5 and as discussed below, fungi were placed on the center of a Potato Dextrose Agar (PDA) plate, and 5 µ/l of bacteria (single or combined strains) streaked out as a single line approximately 3-5 cm away from the fungi and plates were incubated at room temperature.

Antifungal Experiment:

1. Utilizing sterilized knife/spatula aseptically cut out a circle (approximately 0.5 mm radius) of actively growing mycelia (the edge of a growing fungus)

2. Aseptically placed the cut out portion onto a potato dextrose agar (PDA) plate, ensuring the side that has the mycelia directly touching the surface of the fresh agar 3. Aseptically, streak a single line of bacteria of interest approximately 3-5 cm away from the fungus 4. Incubate in room temperature under constant light and monitor the growth of the fungus. If the bacterium is not covered by mycelia of the fungus placed on the centre of the plate, it means the bacterium has an antifungal activity Example 2: Greenhouse Growth Studies Greenhouse study indicated that KGS-3 could enhance disease resistance of wheat against the economically devastating *Fusarium* Head Blight (FHB). Results indicated that in KGS-3 treated wheat samples, *Fusarium* Damaged Kernel (FDK %), which is an indicator of disease severity decreased by ~35% of the control in the susceptible Goodeve cultivar while the yield has increased by ~18% of the control.

Materials and Methods:
Location: Department of Plant Science, University of Manitoba
Design: RCBD (Randomized Complete Block Design)
Crop: Two wheat cultivars, Cardale (moderately resistant) and Goodeve (susceptible to FHB).
Strain: KGS-3.
Treatments (bacterial): KGS-3 applied at two stages (Early and Late) and control (no bacterial inoculation)
Treatment (*Fusarium* head blight fungal isolate): High DON producing or 3-ADON strain applied on the whole experiment at 50% flowering stage to enhance FHB infection
Replication: 6
Growing media: 6" plastic pot filled with the soil mix of peat moss:sand:soil=1:1:1 ratio. Fertilizer used was granular N—P—K (13-12-12).
Timing of bacterial inoculation: at 2-3 leaf stage for early inoculation and at the developmental stage close to anthesis for late inoculation.
Treatment application method: spray inoculum (either bacteria plus *Fusarium*, or *Fusarium* alone) and the control (distilled water) using a hand sprayer onto wheat head at 50% anthesis stage. 50,000 spores per ml concentration of inoculums was prepared. The spores were grown in Carboxy Methyl Cellulose (CMC). The hand sprayer was calibrated so that the desired concentration of spores per plant was deployed. To maintain high relative humidity, the spikes were covered with a glassine bag for 48 hours after inoculation.
Data collected: FHB disease incidence (DI=% infected head) at 21-days post inoculation (dpi); FDK (*Fusarium* damaged kernel–% infected wheat kernel) estimated after harvest; and 100-kernel weight.

These results indicated that the susceptible cultivar Goodeve inoculated with KGS-3 and *Fusarium* showed an estimated mean reduction of 34±4.6% severity compared to the control samples (52±4.6, Table 1). Also, KGS-3 treated samples showed significantly higher yield (2.6±0.2) than the control treatment (2.2±0.2) in the cultivar Goodeve (Table 2).

As can be seen from Table 1 and 2, KGS-3 can be used as a biocontrol agent in FHB resistance. In the above study, the ability of KGS-3 in reducing FHB severity and improving yield has been demonstrated.

The disease incidence decreased when compared to the control for the early KGS-3 treatment, did not change for late KGS-3 treatment. This indicates that earlier application of KGS-3 promotes better resistance, perhaps due to the time required for the bacteria to enter the plant and/or produce enzymes and secondary metabolites that are antifungal.

Example 3: Field Growth Studies

1 Materials and Methods
Location: Carman research station, Manitoba and Kelburn farm, Manitoba
Sites: 3 sites (soil types) in Carman; namely Reinland (south end of block 4), Winkler (block 5e close by the weather station), Denim (NE corner of MacGregor C) and 1 site in Kelburn
Crop: Wheat
Design: RCBD
Treatments: $10^9$ KGS-3 and control (0) CFU/ml
Replication: 4
Climatic conditions: Carman received 172.6 mm while Kelburn received 231.1 mm total rainfall during the crop growing season from May to August 2019. The amount of precipitation one week before and after inoculation were 7.2 mm and 7.6 mm for Carman and 9.1 mm and 3.8 mm for Kelburn, respectively.
Temperature at times of inoculation: 24.3 in Carman and 27.3 in Kelburn.
Soil moisture at time of inoculation: Somehow moist as it rained the previous day 0.7 mm in Carman and 2 days before 2.6 mm in Kelburn.
Next rain after inoculation: 3 days later 5.4 mm precipitation in Carman and 2 days later 2 mm precipitation in Kelburn.

As shown in Table 3, for treatment by location interaction, KGS3 treated samples had relatively higher protein content compared with the control treatment at all locations except in Reinland where the control had the highest (16.9%), the early treated plants had the lowest (16.1%) and the late treated plants had intermediate protein content (16.3%).

The wheat crop was moisture stressed in the 2019 growing season for the PGPB to perform as expected. According to Manitoba Agriculture, an average amount of precipitation required for a wheat plant in a growing season is 275-325 mm. The amount of precipitation received in both locations (172.6 in Carman and 231.1 in Kelburn) were lower than the average required for wheat crop from planting to maturity in Manitoba. KGS-3 showed a slight decrease in yield, which was compensated by an increase in protein No fungal inoculation was done in the field except waiting for natural infection to occur in the field.

Example 4: Growth Conditions

In this example, a single colony of KGS-3 is picked with a sterile plastic loop and used to inoculate 400 mL of LB broth in a 2 liter flask. The flask was then incubated at 30° C., 200 rpm for at least 24 hours and/or until the desired cell concentration was achieved, which can be determined by measuring $OD_{600}$ of a sample of the culture.

Once the desired culture density was achieved, the cells were isolated from the culture media, for example, by centrifugation, for example, by centrifugation at 4700 rpm for 30 minutes. As discussed herein, the supernatant contains antifungal compounds and can be used and/or processed immediately or can be stored at 4° C. for later processing. The isolated or recovered cells, for example, the pellet from centrifugation, can then be diluted in an appropriate volume to attain KGS-3 cells at the desired concentration. For example, the cell pellet can be resuspended in a suitable buffer, for example, phosphate buffered saline, at for example, $1 \times 10^9$ CFU/ml. Other suitable buffers or solutions for resuspension of the cell pellet will be readily apparent to one of skill in the art. As discussed herein, the resuspended cells can then be used for spray-application of KGS-3 to the soil and/or to growing plants and/or suitable carriers, as discussed herein.

Example 5 Chemical Analysis of Secondary Metabolites Produced by KGS-3

KGS-3 was grown in 1 liter of LB at 30° C. centrifuged at 4700 rpm for about 30 minutes and the supernatant was separated. The supernatant was acidified with HCL to PH less than 2. The organic layer from the supernatant was separated in a separatory funnel two times with Ethyl acetate half the amount of the supernatant. The organic layer was evaporated and the crude extract was analyzed with high performance liquid chromatography (HPLC). Several peaks distinct from the secondary metabolites identified from the antiSMASH results mentioned above were identified.

These distinct peaks were resolved into individual fractions on thin layer chromatography (TLC) plates. Initial results from the TLC plate separation showed 11 different compounds. The TLC plates were visualized under UV analysis. The separation of these compounds was done by using flash column chromatography. The compounds were then recovered. Solvent from the recovered fractions was evaporated using a rotary evaporator. The mass of each fraction was recorded and the fractions were stored for further analysis.

During the recovery process, a given fraction might be recovered in multiple tubes. Each test tube was analyzed separately by TLC. Tubes that produced the same results were collected together to results at the end 11 different fractions.

Bioactivity test on all fractions showed that fraction 7 had antifungal activity against *Fusarium graminearum*.

Flash column chromatography was performed on fraction 7 for more purification. The result obtained from LC-MSs was uploaded into the GNPS database. The molecular mass and fragmentation pattern of fragment 7 was compared with all other molecules in NGPS library. Several matches appeared in the search results. One of these, shown in FIG. 13, matched the results from NMR experiments that were done on fraction 7. This molecule is a member of the ilicicolins family of compounds. Illicolins are produced by a number of fungal species and are known to have biological activities against other fungi.

*Paenibacillus polymyxa* strains are known to produce several antifungal compounds. For example, antifungal material that appeared to be mixtures of Fusaricidins have been reported to be produced by *P. polymyxa* (Raza et al., 2008). Fusaricidins are a family of antifungal lipopeptides with a 15-guanidino-3-hydroxypentadecanoic acid (GHPD) as fatty acid side chain and a variable fatty acid part. In another study focused on the effect of Fusaricidin on rot pathogen (*Pestalotiopsis*), it was found to affect energy supply for pathogen growth and disrupted pathogen-related material synthesis (Anming, 2017).

*P. polymyxa* produces LI-F type peptides (AMP-jsa9), a group of cyclic lipodepsipeptides that exhibit broad antimicrobial activity against Gram-positive bacteria and filamentous fungi and were reported to be effective against *Fusarium* diseases in grain (Han et al 2017). Other compounds from *P. polymyxa* that have been shown to have antifungal properties against *Fusarium oxysporum* were the volatile compounds benzothiazole, benzaldehyde, undecanal, dodecanal, hexadecanal, 2-tridecanone and phenol (Raza et al. 2014).

In addition to chemical analysis, the genome analysis of *P. polymyxa* has shown they have genes to produce antifungal compounds Fusaricidin and Paenilarvins (Iturin-Like Lipopeptide Secondary Metabolites) (Luo et al. 2018). Tupinamba et al. 2008 reported that phenazine-1-carboxylic acid (PCA) was the major compound that showed antifungal property in *P. polymyxa* strain SCE2.

Example 6 Petri Plate Assay of KGS-3 Against *F. graminearum*

Four strains of *Fusarium graminearum* isolated from wheat were used in this study. Two low toxin producing strains also known as 15ADON were labeled as 27 and 57. Two high toxin producing strains also known as 3ADON were labeled as 87 and 39.

Revival and Multiplication of the four strains of *Fusarium graminiarum* from freezer stock was done on SNA with 20 ml media poured per plate.

To account for uniform nutrient availability, 20 ml of PDA was poured on each plate used in the experiment testing effect of bacterial strains on the *Fusarium* strains.

First the bacterial strains were tested against fungal strain 57 and 39 i.e. one from the low and one from the high toxin producing fungal strain. KGS-3 showed clearing zone of the fungus on PDA plates incubated for a week at room temperature.

Following this experiment, KGS-3 was further tested on all strains, and compared against an. *E. coli* strain known to have no effect on fungal growth was used as a control to show that the clearing is not because of nutrient depletion but because of the antifungal effect of KGS-3 (FIG. 8).

The breakthrough result proving that KGS-3 is effective in controlling the growth of the fungus was demonstrated on the Petri plate assay on FIG. 6 kept at 4° C. for 60 days (FIG. 9).

Example 7: Anti-Fungal Activity of KGS-3 Supernatant

High toxin producing strain of *F. graminearum* also known as 3ADON was used. For supernatants, equal sized holes were made in the agar plate at equal distance from the center where the fungus disk was placed. A drop of different fractions of the supernatant, prepared as discussed above, was put into each well. KGS-3 supernatant later demonstrated to contain cylidnrol B showed a clearing of fungus around the well (FIG. 10).

Potato dextrose agar (PDA) with specification Difco™ REF 213400 39 g/liter was used to simultaneously grow the bacteria and fungus in the experiment testing effect of bacterial strains on the *Fusarium* strains. PDA was also used to test the fractions against the fungus. To account for uniform nutrient availability, 20 ml of PDA was poured on each plate. Four drops of the fractions dissolved in Acetone were placed at equal distances and the plates were left open until all the fractions evaporated.

After evaporating the solvent, actively growing mycelia of *F. graminearum* was placed at the center of the plate. Utilizing a sterilized knife/spatula a circle was cut out aseptically (approximately 0.5 mm radius) from actively growing mycelia from the SNA plate. The cut out portion was aseptically placed onto a potato dextrose agar (PDA) plate, ensuring the side that has the mycelia directly touching the surface of the fresh agar. The plates were covered with parafilm to prevent drying and contamination. Incubate in room temperature under constant light and monitor the growth of the fungus. If the fraction is not covered by mycelia of the fungus placed on the centre of the plate, it means the fraction has an antifungal activity.

While the preferred embodiments of the invention have been described above, it will be recognized and understood that various modifications may be made therein, and the appended claims are intended to cover all such modifications which may fall within the spirit and scope of the invention.

REFERENCES

Anming Yang, Song Zeng, Lu Yu, Ming He, Yuanyou Yang, Xiaozhen Zhao, Chaolin Jiang, Deyu Hu, Baoan Song, (2017). Characterization and antifungal activity against *Pestalotiopsis* of a Fusaricidin-type compound produced by *Paenibacillus polymyxa* Y-1. Pesticide Biochemistry and Physiology. doi: 10.1016/j.pestbp.2017.08.012.

Bruto, M., Prigent-Combaret, C., Muller, D., & Moënne-Loccoz, Y. (2014). Analysis of genes contributing to plant-beneficial functions in Plant Growth-Promoting Rhizobacteria and related Proteobacteria. Scientific reports, 4, 6261. doi:10.1038/srep06261.

Cheng Z, Park E, & Glick B R. 2007. 1-Aminocyclopropane-1-carboxylate deaminase from *Pseudomonas putida* UW4 facilitates the growth of canola in the presence of salt. Canadian Journal of Microbiology. 53, 912-918.

Cochrane S A, Findlay B, Bakhtiary A, et al. (2016). Antimicrobial lipopeptide tridecaptin A1 selectively binds to Gram-negative lipid II. Proc Natl Acad Sci USA. 113(41):11561-11566. doi:10.1073/pnas.1608623113.

Cosentino S, Voldby Larsen M, Møller Aarestrup F, Lund O. (2013). PathogenFinder-Distinguishing Friend from Foe Using Bacterial Whole Genome Sequence Data. PLoS ONE 8(10): e77302.

Dijksterhuis, J., Sanders, M., Gorris, L. G. and Smid, E. J. (1999), Antibiosis plays a role in the context of direct interaction during antagonism of *Paenibacillus polymyxa* towards *Fusarium oxysporum*. Journal of Applied Microbiology, 86: 13-21.

Eastman, A. W., Heinrichs, D. E., & Yuan, Z. C. (2014). Comparative and genetic analysis of the four sequenced *Paenibacillus polymyxa* genomes reveals a diverse metabolism and conservation of genes relevant to plant-growth promotion and competitiveness. BMC genomics. 15: 851. doi:10.1186/1471-2164-15-851.

Felsenstein J. (1985). Confidence limits on phylogenies: An approach using the bootstrap. Evolution 39:783-791.

Foroud, N. A., McCormick, S. P., MacMillan, T., Badea, A., Kendra, D. F., Ellis, B. E., and Eudes, F. 2012. Greenhouse studies reveal increased aggressiveness of emergent Canadian *Fusarium graminearum* chemotypes in wheat. Plant Dis. 96:1271-1279.

Guo, X. W., Fernando, W. G. D., and Seow-Brock, H. Y. 2008. Population structure, chemotype diversity, and potential chemotype shifting of *Fusarium graminearum* in wheat fields of Manitoba. Plant Dis. 92:756-762.

Han, J et al. (2017). Mechanism of action of AMP-jsa9, a LI—F-type antimicrobial peptide produced by *Paenibacillus polymyxa* JSa-9, against *Fusarium moniliforme*. Fungal Genetics and Biology 104: 45-55.

Helfrich, Eric J. N. et al. (2018). Bipartite interactions, antibiotic production and biosynthetic potential of the *Arabidopsis* leaf microbiome, Nature Microbiology. DOI: 10.1038/s41564-018-0200-0.

Kai Blin, Thomas Wolf, Marc G Chevrette, Xiaowen Lu, Christopher J Schwalen, Satria A Kautsar, Hernando G Suarez Duran, Emmanuel L C De Los Santos, Hyun Uk Kim, *Mariana* Nave, Jeroen S Dickschat, Douglas A Mitchell, Ekaterina Shelest, Rainer Breitling, Eriko Takano, Sang Yup Lee, Tilmann Weber & Marnix H. Medema (2017). antiSMASH 4.0—improvements in chemistry prediction and gene cluster boundary identification. Nucleic Acids Research 45: W36-W41.

Luo Y, Cheng Y, Yi J, Zhang Z, Luo Q, Zhang D and Li Y (2018). Complete Genome Sequence of Industrial Biocontrol Strain *Paenibacillus polymyxa* HY96-2 and Further Analysis of Its Biocontrol Mechanism. Front. Microbiol. 9:1520. doi: 10.3389/fmicb.2018.01520.

Nehra V & Choudhary M. 2015. A review on plant growth promoting rhizobacteria acting as bioinoculants and their biological approach towards the production of sustainable agriculture. Journal of Applied Natural Science. 7, 540-556.

Padda, Kiran Preet & Puri, Akshit & Chanway, Chris. (2017). *Paenibacillus polymyxa*: A Prominent Biofertilizer and Biocontrol Agent for Sustainable Agriculture. 10.1007/978-981-10-5343-6_6.

Parnell J J, Berka R, Young H A, Sturino J M, Kang Y, Barnhart D M, & DiLeo M V. 2016. From the lab to the farm: an industrial perspective of plant beneficial microorganisms. Frontiers in Plant Science. 7.

Puri, K. D., and Zhong, S. 2010. The 3ADON population of *Fusarium graminearum* found in North Dakota is more aggressive and produces a higher level of DON than the prevalent 15ADON population in spring wheat. Phytopathology 100:1007-1014.

Raza, W. Yang W. and Shen Q-R. (2008). *Paenibacillus polymyxa*: antibiotics, hydrolytic enzymes and hazard assessment. Journal of Plant Pathology 90 (3), 419-430.

Raza, Waseem & Yuan, Jun & Ling, Ning & Qiwei, Huang & Shen, Qirong. (2014). Production of volatile organic compounds by an antagonistic strain *Paenibacillus polymyxa* WR-2 in the presence of root exudates and organic fertilizer and their antifungal activity against *Fusarium oxysporum* f. sp. *niveum*. Biological Control. 80. 10.1016/j.biocontrol.2014.09.004.

Saitou N. and Nei M. (1987). The neighbor-joining method: A new method for reconstructing phylogenetic trees. Molecular Biology and Evolution 4:406-425.

Tupinamba et al. 2008. Antimicrobial activity of *P. polymyxa* SCE2 against some mycotoxin-producing fungi. Journal of Applied Microbiology 105: 1044-1053

Yudistira, H (2018). Plant Growth Promoting Properties of KGS Strains and the Formulation of Commercial Inocula. KGS report.

Zhou, Xiao and Huang, Hongbo and Chen, Yuchan and Tan, Jiaheng and Song, Yongxiang and Zou, Jianhua and Tian, Xinpeng and Hua, Yan and Ju, Jianhua (2012). Marthiapeptide A, an Anti-infective and Cytotoxic Polythiazole Cyclopeptide from a 60 L Scale Fermentation of the Deep Sea-Derived *Marinactinospora thermotolerans* SCSIO 00652. J. Nat. Prod. 75(12): 2251-2255

TABLE 1

Lsmean estimates for FDK % in Goodeve and Cardale inoculated with Fusarium in different treatment combinations and controls.

| Genotype | Treatment | Mean + SE |
|---|---|---|
| Goodeve | Control | 52 + 4.6 |
| Goodeve | KGS3 | 34 + 4.6 |
| Cardele | Control | 10 + 4.6 |
| Cardele | KGS3 | 8 + 4.6 |

TABLE 2

Lsmean estimates for Yield (kg/100-kernelweight) in Goodeve and Cardale inoculated with Fusarium in different treatment combination and controls.

| Genotype | Treatment | Mean + SE |
|---|---|---|
| Cardele | KGS3 | 3.4 + 0.2 |
| Cardele | Control | 3.1 + 0.2 |
| Goodeve | KGS3 | 2.6 + 0.2 |
| Goodeve | Control | 2.2 + 0.2 |

TABLE 3

Lsmean estimates of protein content for location by treatment interaction.

| Location | Treatment | Estimate | Standard Error |
|---|---|---|---|
| Winkler | Control | 16.275 | 0.276 |
| Winkler | Late | 17.65 | 0.276 |
| Winkler | Early | 17.35 | 0.276 |
| Reinland | Control | 16.9 | 0.276 |
| Reinland | Late | 16.3 | 0.276 |
| Reinland | Early | 16.1 | 0.276 |
| Denim | Control | 12.6837 | 0.3671 |
| Denim | Late | 13.8 | 0.276 |
| Denim | Early | 13.625 | 0.276 |
| Kelburn | Control | 12.5 | 0.276 |
| Kelburn | Late | 13.35 | 0.276 |
| Kelburn | Early | 13.175 | 0.276 |

The invention claimed is:

1. A method for increasing yield of a plant, increasing protein content of a plant, preventing fungal infection of a plant, or reducing severity of a fungal infection of a plant, the method comprising:
preparing a composition comprising a high-density aliquot of plant growth promoting bacteria KGS-3 *Paenibacillus polymyxa* strain deposited as International Depositary Authority of Canada (IDAC) 120719-01;
applying said composition to a growing plant in a soil environment;
permitting continued growth of said growing plant in said soil environment, said plant growth promoting bacteria KGS-3 *Paenibacillus polymyxa* strain deposited as IDAC 120719-01 inhibiting fungal growth on the growing plant; and
harvesting said plant.

2. The method according to claim 1, wherein the high-density aliquot is applied to leaves of the growing plant.

3. The method according to claim 1, wherein the high-density aliquot is applied to the growing plant after the plant has entered the flowering stage.

4. The method according to claim 1, wherein the high-density aliquot is applied to the growing plant after fungal infection of the growing plant.

5. A method of preventing or reducing the severity of *Fusarium* head blight in a cereal crop comprising:
preparing a high-density aliquot of plant growth promoting bacteria KGS-3 *Paenibacillus polymyxa* strain deposited as IDAC 120719-01;
applying said high-density aliquot to a growing cereal plant, a cereal seedling, or a cereal seed; growing said cereal plant, said cereal seedling, or said cereal seed in a soil environment to produce a cereal crop, wherein said plant growth promoting bacteria KGS-3 *Paenibacillus polymyxa* strain deposited as IDAC 120719-01 inhibits fungal growth on said cereal crop; and harvesting said cereal crop, or
applying said high-density aliquot to a soil environment in which cereal seeds, cereal seedlings or cereal plants have been or will be planted; growing cereal seeds, cereal seedlings and/or cereal plants in said soil environment to produce a cereal crop, wherein said plant growth promoting bacteria KGS-3 *Paenibacillus polymyxa* strain deposited as IDAC 120719-01 inhibits fungal growth on said cereal crop; and harvesting said cereal crop.

6. The method according to claim 5, wherein the *Fusarium* head blight is caused by a fungus selected from the group consisting of *Fusarium avenaceum*, *Fusarium culmorum*, *Fusarium graminearum*, *Fusariuni poae* and *Microdochium nivale*.

7. The method according to claim 5, wherein the cereal crop is selected from the group consisting of wheat, barley, oats, rye and triticale.

8. A method of preventing or reducing the severity of white mold in a plant crop comprising:
preparing a high-density aliquot of plant growth promoting bacteria KGS-3 *Paenibacillus polymyxa* strain deposited as IDAC 120719-01;
applying said high-density aliquot to a growing plant, a seedling, ora seed; growing said plant, seedling, or seed in a soil environment to produce a plant crop, wherein said plant growth promoting bacteria KGS-3 *Paenibacillus polyrnyxa* strain deposited as IDAC 120719-01 inhibits fungal growth on said plant crop; and harvesting said plant crop, or
applying said high-density aliquot to a soil environment in which seeds or seedlings have been or will be planted; growing seeds, seedlings and/or plants in said soil environment to produce a plant crop, wherein said plant growth promoting bacteria KGS-3 *Paenibacillus polyrnyxa* strain deposited as IDAC 120719-01 inhibits fungal growth on said plant crop; and harvesting said plant crop.

9. The method according to claim 8, wherein the white mold is caused by *Sclerotinia sclerotiorum*.

10. A method of preventing or reducing the severity of blackleg in a *Brassicae* plant crop comprising:
preparing a high-density aliquot of plant growth promoting bacteria KGS-3 *Paenibacillus polymyxa* strain deposited as IDAC 120719-01;
applying said high-density aliquot to a growing *Brassicae* plant, a *Brassicae* seed, or a *Brassicae* seedling; growing said *Brassicae* plant, *Brassicae* seed, or *Brassicae* seedling in a soil environment to produce a *Brassicae* plant crop, wherein said plant growth promoting bacteria KGS-3 *Paenibacillus polymyxa* strain deposited as IDAC 120719-01 inhibits fungal growth on said *Brassicae* plant crop; and harvesting said *Brassicae* plant crop, or
applying said high-density aliquot to a soil environment in which *Brassicae* seeds, *Brassicae* seedlings or *Brassicae* plants have been or will be planted; growing *Brassicae* seeds, *Brassicae* seedlings and/or *Brassicae* plants in said soil environment to produce a *Brassicae* plant crop, wherein said plant growth promoting bacteria KGS-3 *Paenibacillus polymyxa* strain deposited as IDAC 120719-01 inhibits fungal growth on said *Brassicae* plant crop; and harvesting said *Brassicae* plant crop.

11. The method according to claim 10, wherein the blackleg is caused by *Leptosphaeria maculans*.

* * * * *